(12) United States Patent
Neftel

(10) Patent No.: US 10,252,045 B2
(45) Date of Patent: Apr. 9, 2019

(54) CONNECTOR CAP ASSEMBLY

(71) Applicant: DEBIOTECH S.A., Lausanne (CH)

(72) Inventor: Frédéric Neftel, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 731 days.

(21) Appl. No.: 14/773,032

(22) PCT Filed: Mar. 4, 2014

(86) PCT No.: PCT/IB2014/059429
§ 371 (c)(1),
(2) Date: Dec. 14, 2015

(87) PCT Pub. No.: WO2014/136050
PCT Pub. Date: Sep. 12, 2014

(65) Prior Publication Data
US 2016/0106969 A1    Apr. 21, 2016

(30) Foreign Application Priority Data
Mar. 4, 2013    (EP) .................................... 13157635

(51) Int. Cl.
| A61M 25/16 | (2006.01) |
| A61M 25/18 | (2006.01) |
| A61M 39/00 | (2006.01) |
| A61M 39/10 | (2006.01) |
| A61M 39/20 | (2006.01) |
| A61M 39/16 | (2006.01) |
| A61M 39/18 | (2006.01) |

(52) U.S. Cl.
CPC ........ *A61M 39/20* (2013.01); *A61M 39/1011* (2013.01); *A61M 39/165* (2013.01); *A61M 39/18* (2013.01); *A61M 2039/1072* (2013.01)

(58) Field of Classification Search
CPC ...... A61M 2039/1072; A61M 39/1011; A61M 39/165; A61M 39/18; A61M 39/20
USPC .......................................................... 604/533
See application file for complete search history.

(56) References Cited

U.S. PATENT DOCUMENTS

| 3,976,311 A * | 8/1976 | Spendlove .......... A61M 39/162 138/89 |
| 6,588,427 B1 * | 7/2003 | Carlsen ............. A61M 16/0463 128/205.12 |
| 7,014,224 B1 * | 3/2006 | Sward ................. F16L 19/0218 285/319 |
| 2004/0260266 A1 * | 12/2004 | Cuschieri ............ A61M 39/045 604/411 |

(Continued)

FOREIGN PATENT DOCUMENTS

WO    WO 03/041789    5/2003

OTHER PUBLICATIONS

International Search Report for PCT/IB2014/059429, dated Jun. 25, 2014, 9 pages.

(Continued)

*Primary Examiner* — Jason Flick
(74) *Attorney, Agent, or Firm* — Nixon & Vanderhye PC (57) ABSTRACT

The invention relates to a connector/cap assembly comprising locking means and coupling means allowing the cap to be removed from the connector using only one hand and preferably without the cap coming into contact with the hand of the practitioner.

33 Claims, 10 Drawing Sheets

(56) References Cited

U.S. PATENT DOCUMENTS

2012/0042971 A1\* 2/2012 Py .................... A61M 39/10
  137/798
2016/0001015 A1\* 1/2016 Kucuk ................ A61M 5/3202
  604/110

OTHER PUBLICATIONS

Written Opinion of the ISA for PCT/IB2014/059429, dated Jun. 25, 2014, 8 pages.

\* cited by examiner

Prior Art

Prior Art

CONNECTOR CAP ASSEMBLY

This application is the U.S. national phase of International Application No. PCT/IB2014/059429 filed Mar. 4, 2014, which designated the U.S. and claims priority to EP 13157635.7 filed Mar. 4, 2013, the entire contents of each of which are hereby incorporated by reference.

FIELD OF THE INVENTION

The invention concerns a connector cap assembly that can be used in many fields of activity that necessitate a certain level of asepsis, connectors in the medical field and an uncapping method. Said invention makes it possible to avoid certain manipulations that would risk contaminating or soiling all or part of the fluid line comprising said connector.

PRIOR ART

Sterile or clean connectors are sometimes used to connect two fluid lines that must remain sterile or clean (for example dust-free) in numerous fields of activity (in particular in the medical field or in industry, for example in white rooms). These connectors may be provided with caps for closing the parts of the connector to be protected in order to prevent contamination or dirt coming into contact with certain parts of the connectors before the connection of said connectors.

As a general rule, when connecting the two connectors, the sterility or "cleanliness" must be ensured in at least the parts protected by the cap and the user must be vigilant as to the sterility or "cleanliness" until the connectors are connected. In other words, when the connectors have been uncapped but not yet connected, the practitioner or the patient must manipulate them with great caution in order to guarantee that they have not unintentionally contaminated the connectors.

Moreover, the connection of two fluid lines may necessitate the use of two separate connectors, each being mounted on a fluid line. To connect them, it is therefore first necessary to uncap the connectors and then, secondly, to connect said connectors together. However, in order not to contaminate or soil the connectors, once uncapped the connectors must not be put down while uncapping the other one. The two connectors must therefore be manipulated together and it is essential to hold a connector at all times when uncapping the other connector. In other words, uncapping must be effected while the two connectors are held by the user, therefore rendering the task more complicated.

By way of example in the medical field, fluid lines must be connected together by any patient suffering renal insufficiency and necessitating peritoneal dialysis at home. In order to avoid the risks of contamination, responsible for infectious peritonitis, certain devices (SleepSafe from Fresenius) recommend automated connection. However, the drawer in which the connectors are placed in order to connect them automatically may be non-sterile, and therefore represent an increased risk of contamination. Other devices include a ring on the external face of the connector (Baxter system) enabling use of one of the fingers of the other hand (generally the little finger) to remove the cap while each hand is holding a respective line to be connected. Such a system does not guarantee the absence of contamination given the proximity of the fingers to the interior portion of the connector and makes it difficult to explain the manipulations to the patient.

The PCT application published under the number WO 94/28855 A1 and U.S. Pat. No. 4,573,980 A disclose a cap enabling prevention of contact of any element with the initially protected portion of the connector. Thus the cap includes a ring into which a finger can be slid. Thanks to this ring, the connector can be uncapped by pulling on this ring. The practitioner therefore does not touch the protected part of the connector. FIGS. 1a to 1c and 2a to 2c show in more detail the manipulation necessary for uncapping and connecting the connectors.

Figure 1A:
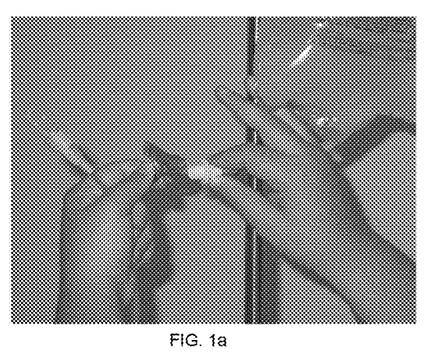
FIGS. 1a to 1d and 2a to 2d show the use of prior art connectors
Figure 1B:
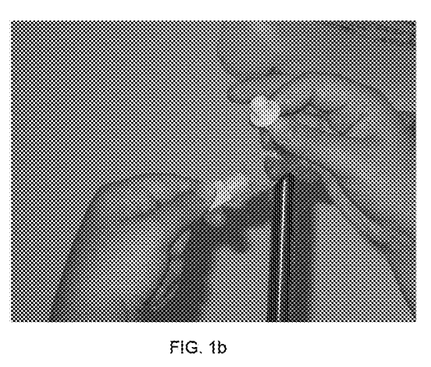
Figure 1C:
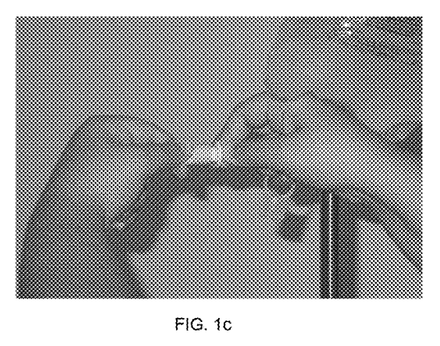
Figure 1D:
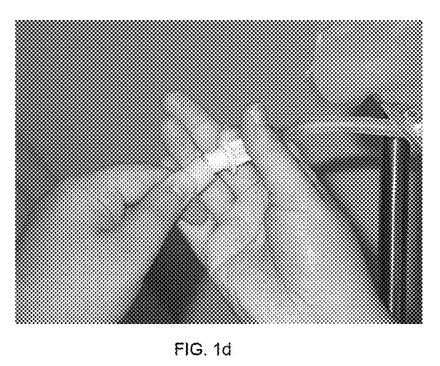

FIG. 1a shows two connectors, the first held in the left hand of the practitioner and the second in their right hand. The second connector is uncapped while holding said connector with the thumb and the index finger while the other fingers of the right hand remain far away from the connector, these fingers then forming a "butterfly wing". The left hand holds the first connector while removing the cap from the second connector. In FIG. 1b, the first connector is uncapped (using the ring) by the right hand which at the same time holds the second connector, which has already been uncapped. In FIG. 1c, the two connectors are connected while keeping the hands and fingers as far away as possible from the distal end of the connectors. FIG. 1d shows a way of connecting them that is proscribed because there is a risk of the fingers contaminating the connectors.

Figure 2A:
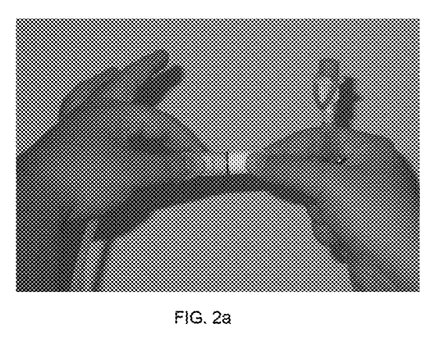
Figure 2B:
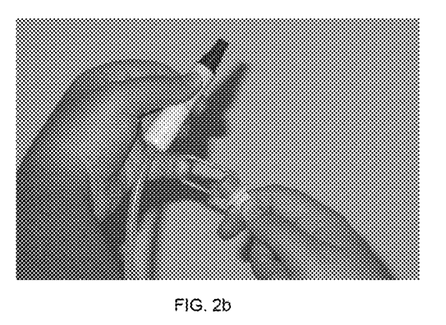
Figure 2C:
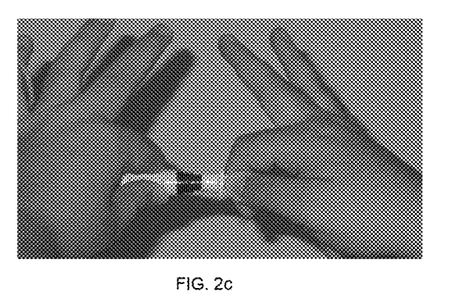
Figure 2D:
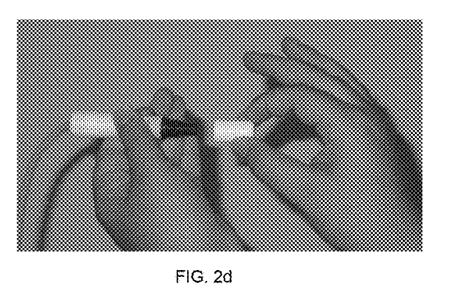

FIGS. 2a to 2d show another connector/cap assembly. In FIG. 2a, while uncapping the first connector, the left hand holds the first connector, forming a butterfly wing, and the right hand unscrews the cap from the first connector, while holding away the second connector fitted with its cap. In FIG. 2b, the first connector is uncapped and held so as not to contaminate the portion initially protected by the cap at the same time as pulling the cap off the second connector using the ring of the latter and one finger of the left hand, preferably the little finger. In FIG. 2c, the two connectors are connected with the fingers of both hands forming butterfly wings in order to be sure not to contaminate the connectors. FIG. 2d shows a manipulation that is proscribed in which the fingers of the left hand may contaminate the initially protected portion of the first connector when the latter is uncapped.

To summarize, the PCT application published under the number WO 94/28855 A1 and U.S. Pat. No. 4,573,980 A disclose a type of connector that must be held by one hand and uncapped by the other one, whilst paying attention to the placement of the fingers. The risks of contamination during manipulation are therefore numerous and the connection method difficult or even laborious. The practitioners must imperatively be trained in these manipulations, which are not obvious.

Some patents claim connector/cap assemblies that enable the connectors to be held while uncapping them. For example, the PCT application published under the number WO 83/00622 A1 and European patent EP 0 621 053 B1 disclose caps fixed to the connectors by hinge means. These connectors can be uncapped merely with the thumb and closed again. However, the connector not always including means protecting against contact of the thumb with the portion initially protected by the cap, the thumb may contaminate the connector during this manipulation. In fact, in pushing on the cap, the thumb may come into contact with the initially protected portion or come near said portion and therefore contaminate it. Moreover, such a system does not indicate if the connector has already been used or merely uncapped temporarily. The connector may therefore have been contaminated without the practitioner knowing it. This type of device is therefore unable to ensure that the connectors are not contaminated. To summarize, this connector can therefore be held and uncapped with one hand, but there is a high risk of contamination by the practitioner or the patient.

Another type of connector, disclosed by the International application WO 03/041789 A1 or US 2012/042971 A1, enables the user to avoid touching the cap because it continues to be retained on or in the connector when the two connectors are connected to each other. However, given that the cap remains connected to the connector or in the enclosure of the connector, it remains near the fluid path, which generates a high risk of direct or indirect contamination.

Indirect contamination is to be understood as contamination of the fluid line following a contaminated element coming close to the fluid line and being able to transmit this contamination to it. With particular reference to the two devices of the documents cited above, the caps remain in an enclosure near the fluid line and can therefore transmit contamination to the fluid line. More particularly, if the caps of the device from the application WO 03/041789 A1 are not positioned correctly in the space provided for this purpose, there is a risk of the fluid line hitting these caps when connecting the fluid lines, causing deterioration of said passage, weakening of the seal of this passage and/or contamination of the passage.

In the light of these observations, new devices have been created based on the premise that manipulation by the practitioner represents a high risk factor. Thus the PCT application published under the number WO 2009/006507 A1 discloses an automatic device for uncapping the connectors and connecting the fluid lines without the assistance of the practitioner. However, this kind of device has proved not to ensure the sterility of the connectors. In fact, the elements that protect the connection system cannot be sterilized after each use and these protection elements can therefore lead to much greater propagation of the contamination than the manual system.

Manipulation by the practitioner or the patient therefore remains the best way to guarantee non-contamination of the assembly. However, the manipulation of the existing devices remains laborious and non-obvious, generating numerous risks of contamination. Moreover, some devices are extremely complicated, making their manufacture too costly, without guaranteeing satisfactory cleanliness. These types of device may therefore not be economically viable.

GENERAL DESCRIPTION OF THE INVENTION

An object of the present invention is to produce a sterile capped connector the manipulation of which is simplified and the manufacturing cost of which is limited, and the invention makes it possible to eliminate the drawbacks of the known connectors cited above.

The present application claims the priority of EP 13157635.7 filed 4 Mar. 2013 in the name of DEBIOTECH SA, the entire content of which is to be considered as forming part of the present application.

The present invention is described and characterized by the independent claim or claims, while the dependent claims describe other features of the invention.

The present document describes a connector/cap assembly in accordance with a first aspect of the invention that can be used in the medical field and also in the industrial field when a certain level of cleanliness is required, for example in white rooms. Said connector comprises a body including a proximal end connected to a fluid line and a distal end fashioned to enable connection with another connector or another system/device. The body is moreover composed of a fluid flow passage enabling a fluid connection between said fluid line and another fluid line to which the connector can be connected. The cap protects at least said passage so as to keep said passage clean and/or sterile.

Said cap and/or said connector comprise locking means enabling said cap to be firmly secured to said connector at least temporarily. Said cap and/or said connector are fashioned so that they can be separated before the connector is connected to another fluid line, for example to another connector or connection system. This therefore makes it possible to guarantee that the cap is no longer present in a so-called safety enclosure so as to prevent indirect contamination coming for example from the cap. In one embodiment, the cap protects the flow passage and can also protect the connection means enabling the connector to remain fastened to another connector or connection system.

In the present document, the word "enclosure" is to be understood as referring to a space the boundaries of which may be material or not and which may change or not. A safety enclosure therefore represents a space within which cleanliness and/or sterility must be maintained. The safety enclosure includes the fluid flow passage and also an additional passage making it possible to prevent any indirect contamination caused by the cap or the hand of the user when manipulating the connector. In one embodiment, when the cap is on the connector at least a portion of the internal surface of the cap delimits the safety enclosure and when the connector is connected to a fluid line the safety enclosure is delimited by the connector and the device to which the connector is connected. The external surface of the cap is in direct contact with the exterior environment and must therefore imperatively remain outside the safety enclosure when the cap is not protecting the flow passage.

The assembly comprises means providing a simple way to uncap the connector preventing all contamination of the portions to be protected (in particular the safety enclosure). These means may comprise ejection means, release means, coupling means and/or any other means enabling the connector to be uncapped easily. Said means may for example make it possible to uncap said connector with only one hand or to uncap a connector using another connector/cap assembly or another device such as an uncapping device.

Said connector cap assembly may also comprise a retaining device in order for the cap to remain connected to the connector but sufficiently far away from the safety enclosure for the cap not to be able to contaminate the flow passage of the connector either directly or indirectly.

The document describes a connection system in accordance with a second aspect of the invention comprising two connector/cap assemblies. Said caps are designed to be separated from their respective connector without being touched directly by the user. In one preferred embodiment, the connectors comprise a body designed to be held by the user whereas the caps are not designed to be held by the user. Also, each connector/cap assembly is designed to be uncapped while the hands of the user hold only the connector bodies.

In one embodiment, the caps are designed to be separated from their respective connector before the connectors can be connected together. In other words, the caps prevent physical connection of the connectors. By physical connection of the connectors is to be understood: physical connection between two connectors enabling them to be held together to ensure firmer and safe retention, the connection means may be coupled to locking elements. The locking elements may form part of the locking means that retain the caps on the connectors.

Thus in this embodiment the caps both protect the flow passages and prevent connection of the connectors. This embodiment makes it possible to avoid direct and indirect contamination of the flow passage because it makes it possible to be sure that any element that may be contaminated (for example the caps, the hands of the user) are sufficiently far away from the safety enclosure (and therefore the fluid flow passages) when connecting the connectors to each other. Moreover, thanks to this embodiment, any user understands that when the two connectors are connected together the fluid connection is made and safe.

In one embodiment, at least one physical connection means delimits the safety enclosure when the two connectors are connected.

In one preferred embodiment, the fluid connection (i.e. the connection of the fluid flow passages of the two connectors) and the physical connection of the connectors are effected in one and the same step. This makes it possible to minimize the number of steps, to limit complexity of the connectors and to facilitate their use.

LIST OF FIGURES

To enable a better understanding of the invention, there will be described one or more embodiments illustrated by the figures appended to this document.

It goes without saying that the invention is not limited to these embodiments.

LIST OF REFERENCE NUMBERS USED IN THE FIGURES

1 Connector cap assembly
2 Fluid line
3 Connector
4 Cap
5 Connector distal end
6 Connector proximal end
7 Cap distal end
8 Cap proximal end
9 Connector body
10 Cap body
11 Coupling means
12 Connector system
13 Locking means
14 Retaining means
15 Release means
16 Trigger
101 Female cap/connector assembly (first assembly)
102 Male cap/connector assembly (second assembly)
103 Female connector (first connector)
104 Male connector (second connector)
105 Female connector cap (first cap)
106 Male connector cap (second cap)
107 Connector body
108 Membrane
109 Thread
110 Passage
111 Proximal end
112 Distal end
113 Fin
114 Lug
115 Cylindrical element
116 Coupling means
117 Slot
118 Leaf spring
119 Stop
120 Projecting element on leaf spring
121 Cap distal end
122 Cap proximal end
123 Principal axis
124 Stop
201 Female cap/connector assembly (first assembly)
202 Male cap/connector assembly (second assembly)
203 Female connector (first connector)
204 Male connector (second connector)
205 Female connector cap (first cap)
206 Male connector cap (second cap)
207 Connector body
208 Membrane
209 Physical connection means
210 Fluid connection means
211 Connector proximal end
212 Connector distal end
213 Cap locking means
214 Connector locking means
215 Cap distal end
216 Cap proximal end
217 Cap retaining device
218 Holding means
219 Fluid flow passage
220 Tube

DETAILED DESCRIPTION OF THE INVENTION

In the present document, the detailed description of the invention covers embodiments of devices, systems and methods described by way of illustration. Clearly other embodiments can be envisaged and may be added without departing from the scope or the spirit of the invention. The following detailed description should therefore not be understood in a limiting sense.

Unless otherwise indicated, the scientific and technical terms used in the present document have the meanings routinely used by the person skilled in the art. The definitions added in this document are referred to in order to facilitate the understanding of the terms frequently used and are not intended to limit the scope of the invention.

The indications of direction used in the description and the claims, such as "top", "bottom", "left", "right", "upper", "lower" and other directions and orientations are referred to in order to clarify references to the figures. These indications are not intended to limit the scope of the invention.

In the present document, the expression "distal end" is to be understood as the end farthest from a reference. In particular, if the reference is the fluid line of the connector, the distal end of a connector is the end that is farthest from its fluid line. This end may equally be referred to as the "free" end because, in contrast to the proximal end, it is not directly connected to the fluid line. Moreover, the distal end of a cap is the end that is farthest from the fluid line.

Conversely, the expression "proximal end" is to be understood as the end nearest a reference. The proximal end of a connector is therefore the end that is directly connected to its fluid line and the proximal end of a cap is the end nearest the fluid line of the connector.

When the cap covers at least the distal end of the connector, the distal end of the cap and the proximal end of the connector therefore represent the opposite ends of the connector/cap assembly. The distal ends of the connectors are preferably fashioned in such a manner as to enable the connection between two compatible connectors. In one embodiment, this connection is possible only when the caps are removed from the distal end of the connectors.

The term practitioner is to be understood in the broad sense as the person trained to manipulate the connectors and includes a member of the medical profession or possibly a patient.

Figure 3:
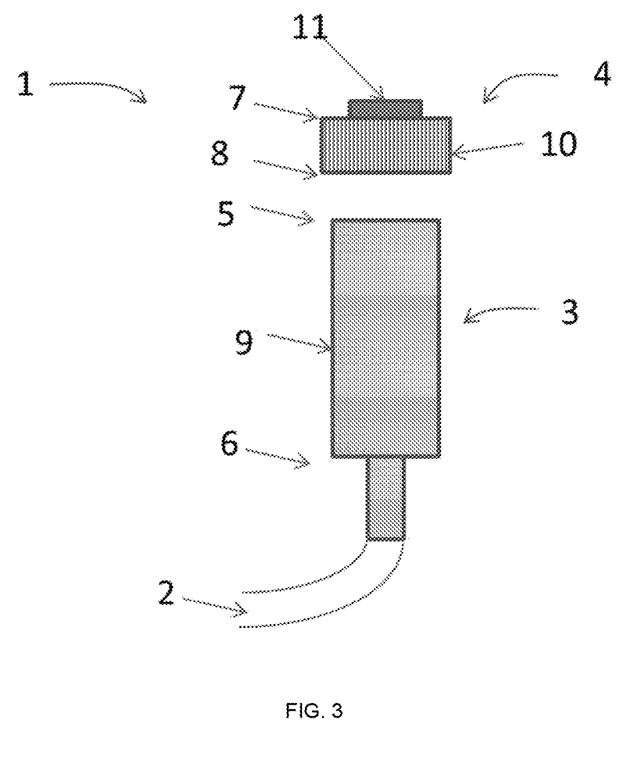
FIG. 3 shows diagrammatically a connector cap assembly

In an embodiment shown in FIG. 3, the connector/cap assembly (1) comprises a connector (3) and a cap (4). Said connector (3) includes a body (9) defining a fluid flow passage protected by said cap (4) disposed at the distal end (5) of said connector (3). The assembly (1) comprises locking means (not shown in FIG. 1) designed to retain the cap (4) firmly on the connector (3) at least temporarily. The cap (4) further comprises coupling means adapted to couple said cap with an element also including coupling means. Said coupling means (11) preferably enable coupling at least while the practitioner deactivates the locking means in order to uncap said connector (3) without having to "touch" the cap (4).

In one embodiment, the cap (4) is coupled to another device or system. For example, if the connector is used in the context of a dialysis treatment, the dialysis device may also comprise coupling means so that the cap (4) is coupled to the dialysis device in order to enable uncapping of said connector.

Figure 4A:
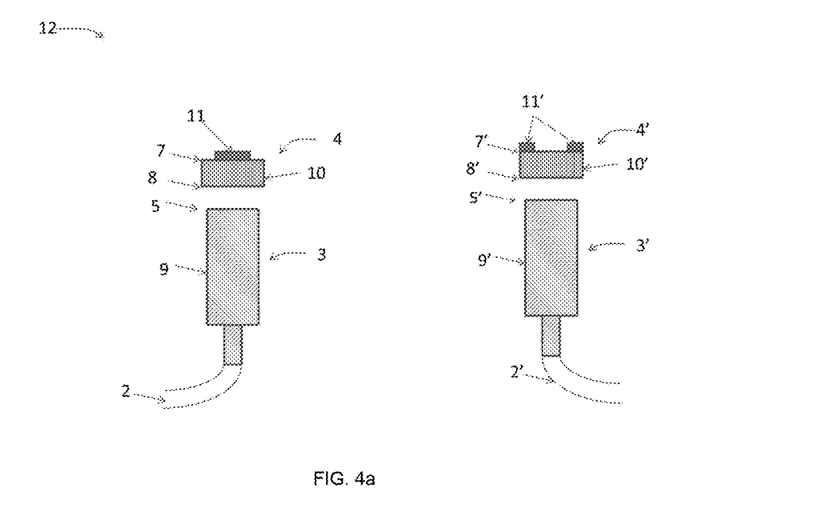
FIG. 4a shows diagrammatically a connector system
Figure 4B:
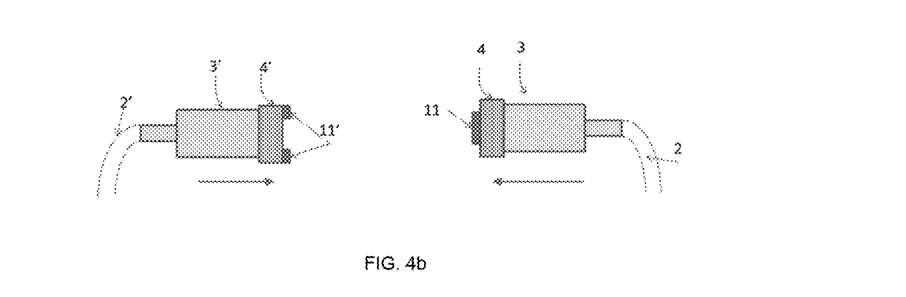
FIGS. 4b to 4d show diagrammatically the actions necessary for uncapping
Figure 4C:
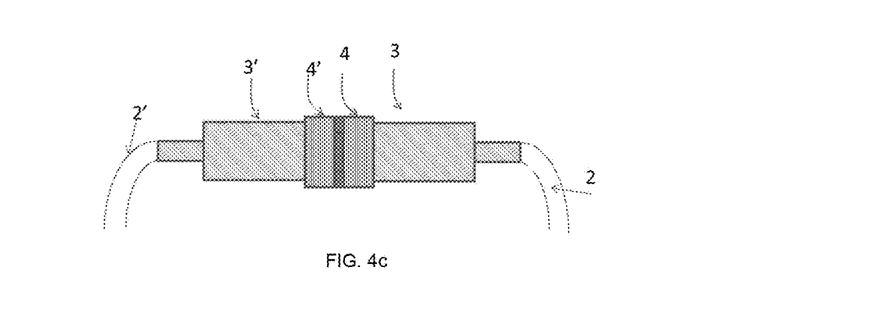
Figure 4D:
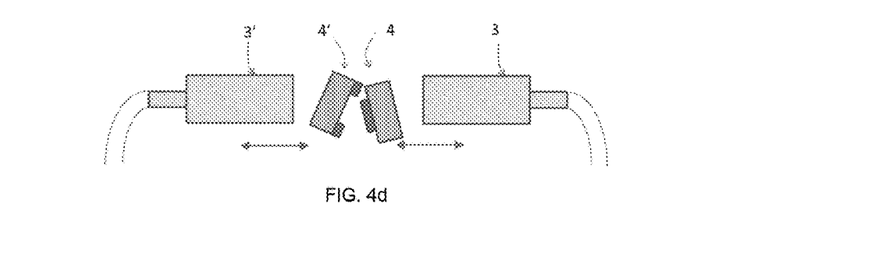

In an embodiment shown in FIG. 4a, a connection system (12) comprises two separate connectors (3, 3') enabling connection of two fluid lines (2, 2'). The distal ends (5, 5') of said connectors (3, 3') are designed to enable the connection of said connectors (3, 3'). Moreover, said distal ends (5, 5') may be of identical or different but compatible shapes, for example, one of male type and the other of female type. The connectors comprise connection means (not shown in FIG. 4), to enable retention of the two connectors. The caps (4, 4') comprise coupling means (11, 11') fashioned to couple the two caps (4, 4') together. FIGS. 4b to 4d show the manipulation for uncapping the connectors. In FIG. 4b, the practitioner can hold a connector in each hand by the body (9, 9') of said connector (3, 3'). The two connectors (3, 3') must move toward each other in order for the two caps (4, 4') to be coupled together (see FIG. 4c). The physical connection means may be operative or used only after uncapping the connectors.

The bodies (9, 9') may comprise holding means enabling the practitioner to hold the connectors by the bodies.

In one embodiment, the connectors are formed of a single part comprising a body:
designed to be held by the hand of a practitioner, and
defining a fluid flow passage.

The body may also comprise connection means, locking elements (for keeping the connectors connected) and/or locking means (for holding the caps against the connectors). This single part may be produced by a manufacturing process such as injection molding, molding, sintering or machining.

In one embodiment, an assembly (1) may further comprise release means (not shown) that are activated as soon as the caps come into contact and/or are coupled in such a manner as to release at least one cap from its connector (3, 3').

In one embodiment, the unlocking mechanism is activated by the practitioner, for example by a movement of rotation of at least one connector (3, 3') on its principal axis.

In one embodiment, after unlocking the locking means of at least one assembly, the practitioner drops at least one cap. FIG. 4d shows diagrammatically caps (4, 4') that do not remain coupled after unlocking. However, in one embodiment, the coupling means (11, 11') can enable the caps (4, 4') to remain fastened at least temporarily after unlocking the caps.

Said coupling means (11, 11') may be magnets and/or fashioned like a hook or some other shape enabling coupling of said caps to each other.

In one embodiment, the coupling means (of the cap or caps or of said device cited in the above example) include a coding system so that only compatible codings enable the cap to be coupled. Said coding possibly enables certain caps to be coupled to a series of other caps, while certain caps can be coupled only to a smaller number of caps.

Figure 5:
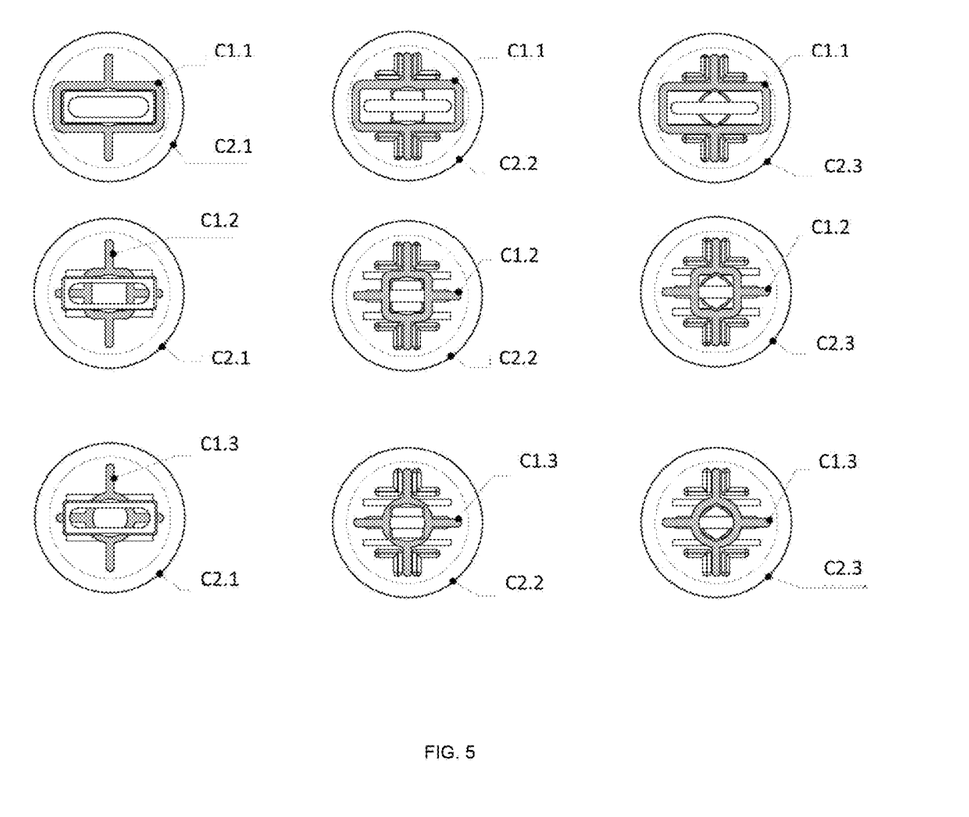
FIG. 5 shows different codings of the coupling means

FIG. 5 shows the various possible combinations between the various coupling means. Thus the coupling means C1.1 are compatible with the coupling means C2.1, C2.2 and C2.3 of the cap and/or other system/device. This means that the connector having a cap having coupling means of C1.1 can be connected to a system and/or connector having a cap having coupling means of C2.1, C2.2 or C2.3 type. Similarly, C1.2 is compatible with C2.2 and C2.3 but incompatible with C2.1. And C1.3 is compatible with C2.3 but incompatible with C2.1 and C2.2.

In accordance with one embodiment, the coupling means are adapted to be nested, for example a first coupling means comprises a female element and a second coupling means comprises a male element compatible with the first coupling means. The coupling means are preferably designed to resist rotation stresses.

This coding therefore makes it possible to avoid all connection errors because the incompatible codings do not allow the connectors to be uncapped and, in one embodiment, the incompatible codings therefore make it impossible to connect the connectors. For example, when one connector comprises connection means of female type and the other (connector) of male type, a connector cap comprising male type connection means could not be coupled with another connector cap comprising connection means of male type. Another example: if two fluid lines cannot be compatible, then the coding system can prevent the connection between these two fluid lines because it will be impossible to remove the caps.

In addition to the coding system that enables coupling, the connector cap assembly may comprise safety elements. These safety elements have to be bypassed (neutralized) to unlock the caps. Also, the coding system makes it possible to neutralize the safety element so that even if the practitioner succeeds in coupling them forcibly, the coding system prevents bypassing the safety feature.

In one embodiment, at least one connector (3, 3') and/or at least one cap (4, 4') comprise drive means to move the cap at least partially away from the connector when the locking means are deactivated. These drive means can make it possible to eject the cap so that the practitioner does not need to effect any other manipulation to release the connector or simply to move the cap so that the practitioner has only to orient the distal end of the connector downward for the cap to fall off.

In one embodiment, the locking means are destroyed by a manipulation by the practitioner so that the cap is detached from the connector. This embodiment prevents connectors that have already been used from being capped again, so that it is easy to tell and obvious when a connector has already been used or simply that the cap has already been removed (which does not guarantee the cleanliness of the connector).

In one embodiment, the locking means comprise at least one safety element so as to prevent unintentional deactivation of the locking means. This safety element may necessitate a minimum force or a specific manipulation to be deactivated/removed.

Figure 6:
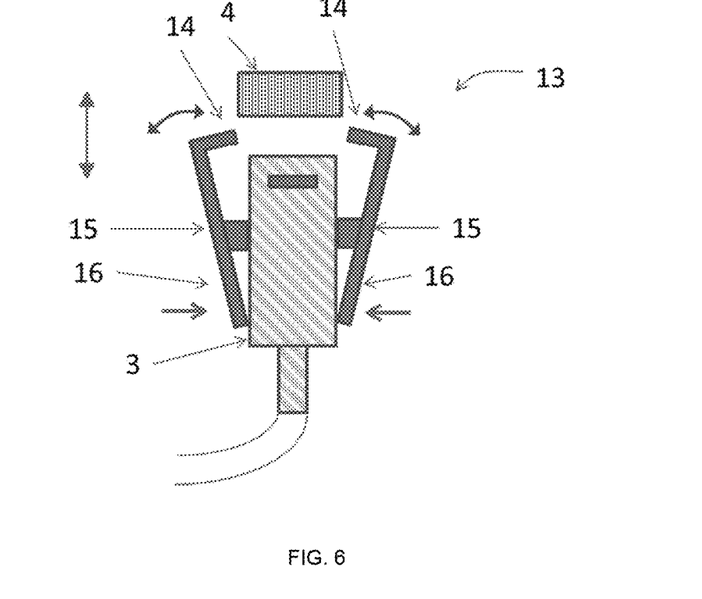
FIG. 6 shows diagrammatically another embodiment of a connector cap assembly

In an embodiment shown diagrammatically in FIG. 6, the locking means (13) comprise retaining means (14) adapted to hold the cap (4) against the connector (3) and release means (15) that can be activated by a trigger (16). A safety element may be disposed so as initially to retain the trigger (16). In this conceptual figure, the pivot represents the release means (15), applying a force against the trigger (16) represented by the arm of the locking means (13), the hook-shaped retaining means (14) of being moved to release the cap (4). In this embodiment, the connector cap assembly may also comprise a spring or other drive means such as a leaf spring that would make it possible to eject or to move the cap (4) when the locking means (13) are deactivated. The cap (4) may equally comprise coupling means. Said trigger (16) and/or the safety element may be arranged on and/or in the cap and/or the connector.

In one embodiment, the release means are activated by exerting a force on the exterior face of the distal end of the cap in the direction of the connector and the drive means are adapted to move said cap away from said connector at least after activation of the release means.

Figure 7:
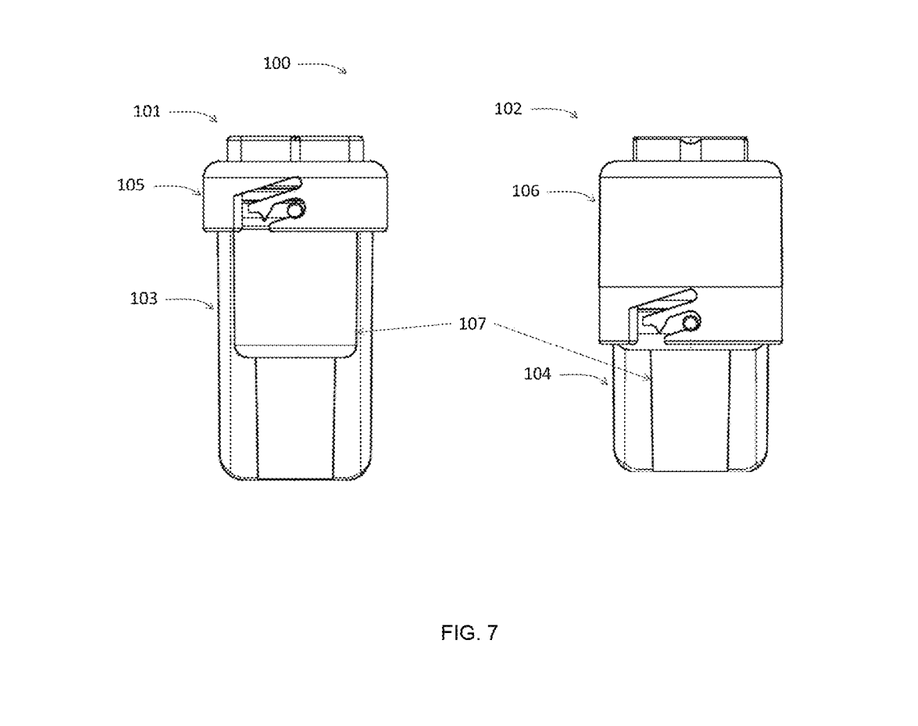
FIG. 7 shows another embodiment of a connector system

The following description applies to a specific embodiment shown in FIGS. 7 to 11:

FIG. 7 shows the connector system (100), which comprises a first assembly (101) composed of a female type connector (103) also referred to as the first connector and an associated cap (105) also referred to as the first cap as well as a second assembly (102) composed of a male type connector (104) also referred to as the second connector and an associated cap (106) also referred to as the second cap.

Figure 8A:
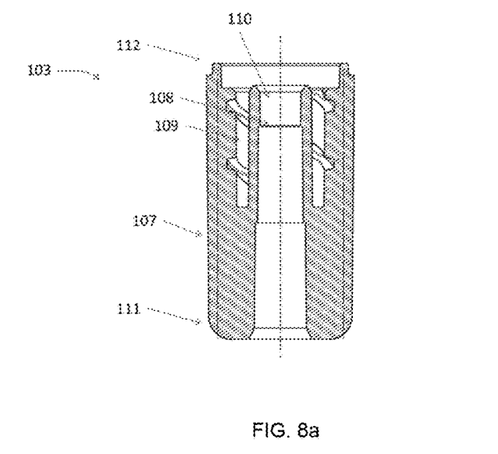
FIGS. 8a to 8c show a different view of the female connector and its cap

FIG. 8*a* shows a cross section of the first connector (103) composed of a body (107) through which passes a passage (110). The proximal end (111) of the connector (103) is permanently connected to a fluid line (not shown). The passage (110) may be closed by a membrane (108) that can be pierced, torn and/or opened by another connector, system or device.

Figure 9A:
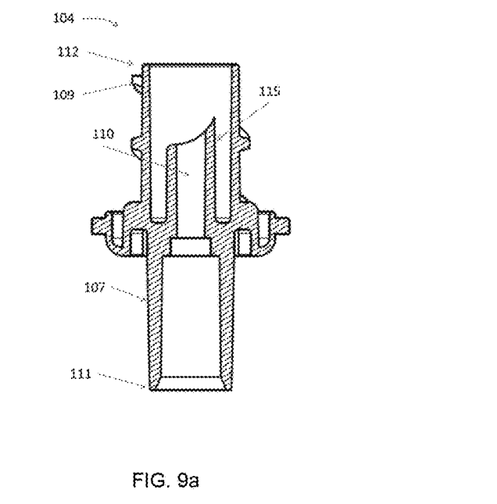
FIGS. 9a to 9c show a different view of the male connector and its cap

FIG. 9*a* shows a cross section of the second connector (104) composed of a body (107) through which passes a passage (110). The proximal end (111) of the connector (104) is permanently connected to a fluid line (not shown). Said passage (110) of the second connector (104) may comprise a cylindrical element (115) that can enter the passage (110) of the first connector (103). Said cylindrical element (115) may have a pointed end so as to pierce or open the membrane (108) of the first connector (103).

Figure 8B:
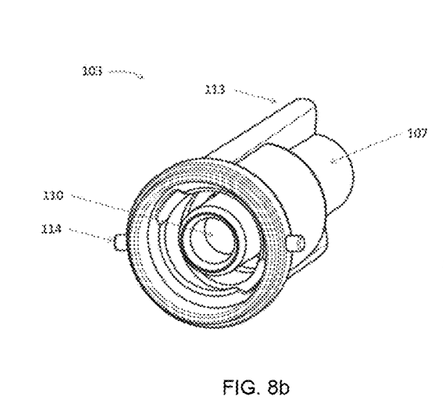
Figure 9B:
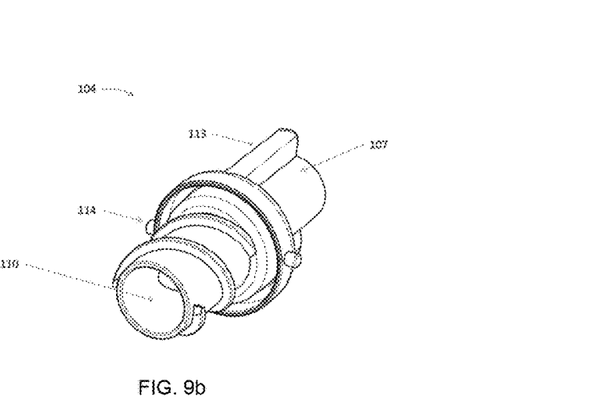

FIGS. 8*b* and 9*b* show a perspective view of the connectors (103, 104). Said connectors (103, 104) may comprise holding means projecting from their body (107) in order to form fins (113) that make it possible to facilitate manipulation of said connectors (103, 104). Said connectors (103, 104) may further comprise lugs (114) fashioned to cooperate with the locking means.

Figure 8C:
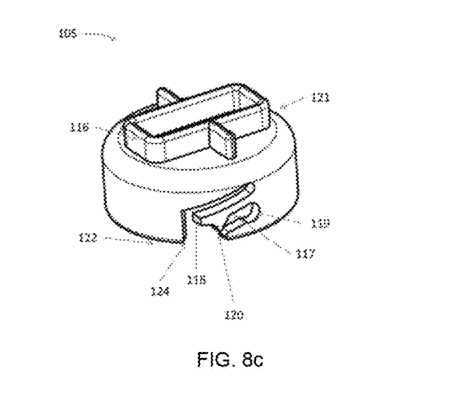
Figure 9C:
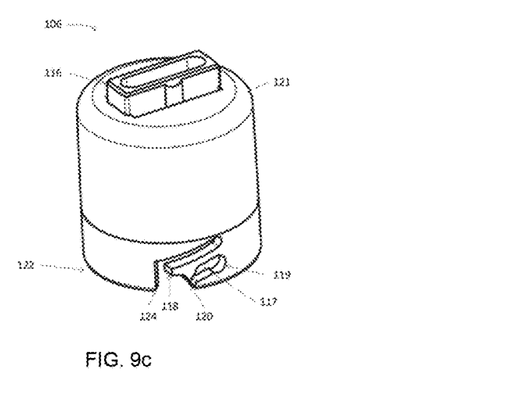

FIGS. 8*c* and 9*c* show a perspective view of the caps (105, 106) of said connectors (103, 104). The cap (105, 106) comprises coupling means (116). In one embodiment, said cap (105, 106) comprises the locking means, which may be composed of at least one slot (117) extending from the proximal end (122) of the cap as far as a stop (119). Said slot (117) may be straight and/or curved. The thickness of at least one slot (117) is at least equal to the width of the lug (114) so that the lug (114) can slide in said slot (117). Said stop (119) may be fashioned to immobilize said lug (114) at least temporarily. Said slot may comprise or be composed of a leaf spring (118) that can include a projecting element (120) so as to immobilize said lug (114) of the connector (103, 104) between the projecting element (120) and said stop (119). Said slot (117) may contain a second stop (124) opposite the first stop (119) and disposed near the proximal end (122).

In another embodiment, the lugs may be arranged on the cap and the locking means on the connector.

In one embodiment, the locking means may comprise a thread system disposed on the caps (105, 106) and/or the connectors (103, 104); said thread system is configured so that it can be coupled and may be composed of at least one lug, one thread and/or a multitude of threads.

Figure 10:
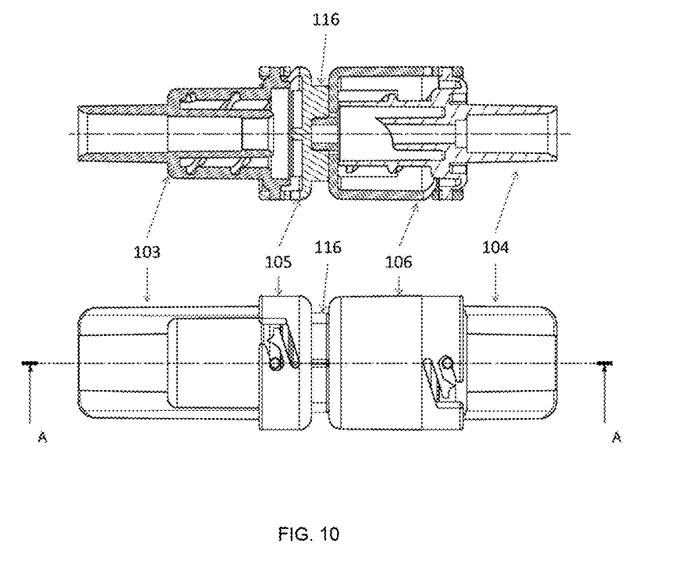
FIG. 10 shows a connector system coupled by the caps

In FIG. 10, the two caps (105, 106) are mounted on and locked to their respective connector (103, 104). The two caps are coupled to each other by the coupling means (116).

Figure 11:
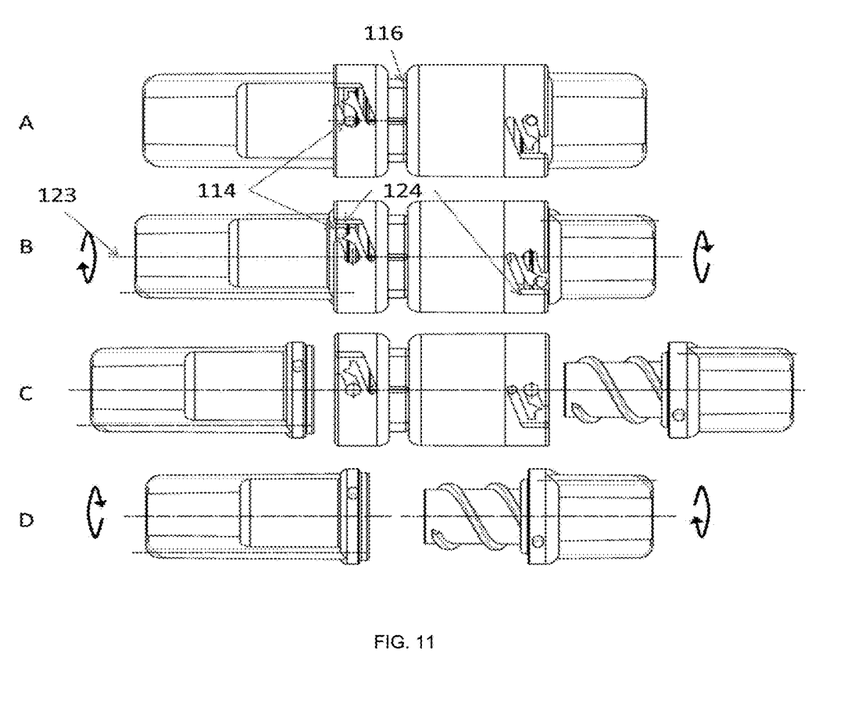
FIG. 11 shows diagrammatically the actions necessary for uncapping and connecting the connectors

FIG. 11 shows the manipulation necessary to uncap and connect the connectors. In phase A, the two connectors (103, 104) fitted with their respective cap (105, 106) are moved toward each other in order to couple the two caps (105, 106) together. During this phase the lugs (114) lie against the stop (119) of the slot (117). In phase B, the practitioner causes pivoting of the system on the longitudinal axis (123). The first and second connectors are facing each other and so the hands holding the bodies of the connectors must effect a rotation enabling unlocking of the caps. The caps (105, 106), being retained by the coupling means, are fastened together and subjected to the forces causing the connector to rotate. The lugs (114) therefore slide in the slot (117) as far as the element (120) projecting on the leaf spring (118). In accordance with this embodiment, an additional force may be applied in order to flex the leaf spring (118) so that at least one lug (114) can be released from the slot (118). The second stop (124) makes it possible to retain the released lug (114) so that the lug (114) of the other cover (105, 106) can be released. In phase C, the caps (105, 106) are unlocked from their connector (103, 104). It then suffices to move the two connectors (103, 104) apart and to allow the caps (105, 106) to drop off. In one embodiment, the leaf spring (118) also acts as drive means in order to push the cap (105, 106) off its connector (103, 104) or even to eject it. In phase D, the two connectors (103, 104) are moved toward each other and connected. In one embodiment, the connectors (103, 104) comprise a thread system fashioned so that it can be coupled. The connection may be effected by a rotation in the opposite direction to that of the step B. In one preferred embodiment, the cap unlocking rotation angle may be substantially equal to the rotation angle for connecting the connectors but in the opposite direction. In one embodiment, said thread system that enables coupling of the connectors is also used to couple the connectors to their respective caps.

In other words, the connector/cap system is designed to avoid the user touching the caps to remove them. Moreover, in order to limit indirect contamination, the connector/cap assembly is designed to force uncapping of the connectors before connecting them to each other so as to move the caps away from the flow passage. This is therefore a two-fold precaution that substantially reduces the risks of direct and indirect contamination.

In one embodiment, the projecting element (120) on the leaf spring (118) is fashioned so that the released lug (i.e. the cap unlocked from its connector) cannot return to its initial position against the first stop (119). In other words, once unlocked, the projecting element (120) on the leaf spring (118) prevents the cap (105, 106) from being locked to its connector (103, 104) again. For example, the shape of said element (120) may prevent reverse movement or the leaf spring (118) may break so that the cap (105, 106) can no longer hold the connector (103, 104) or be locked to it again.

This embodiment is particularly pertinent with regard to avoiding touching the cap. In fact, a simple and intuitive manipulation enables uncapping of the connectors. Moreover, it is possible to connect the connectors in a certain and clean manner without having to change the position of the fingers on the connector.

Figure 12:
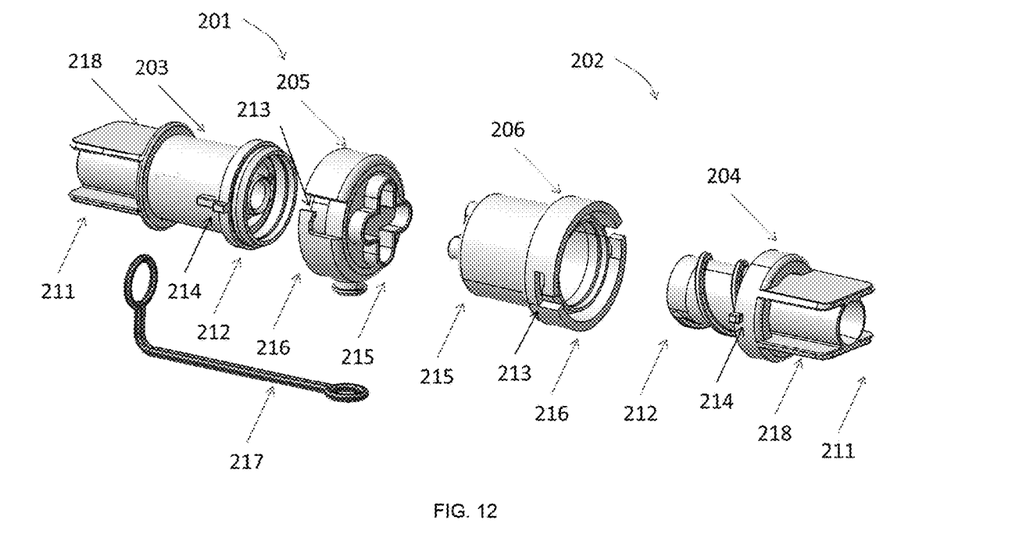
FIG. 12 is an exploded view of one embodiment of a connection system
Figure 13:
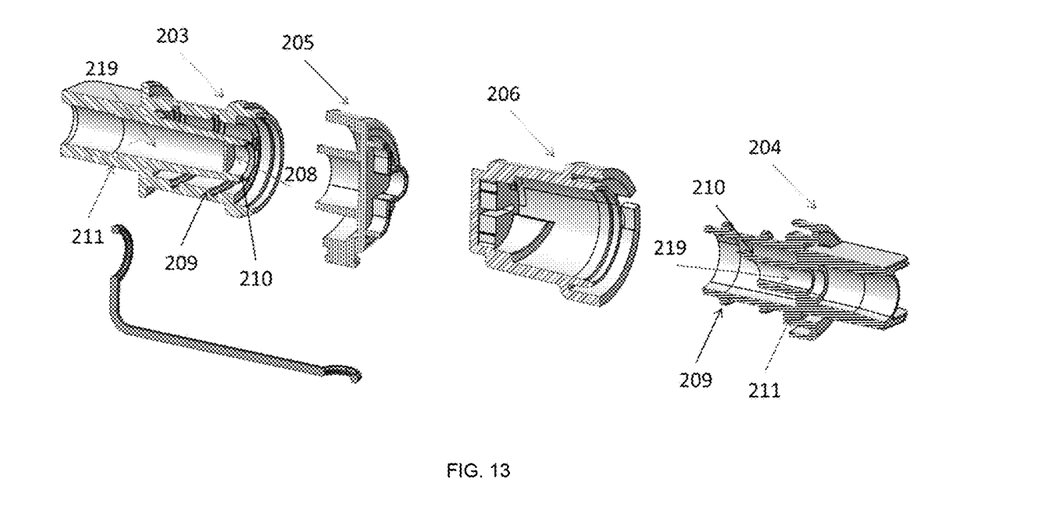
FIG. 13 shows a section of the elements shown in FIG. 12
Figure 14:
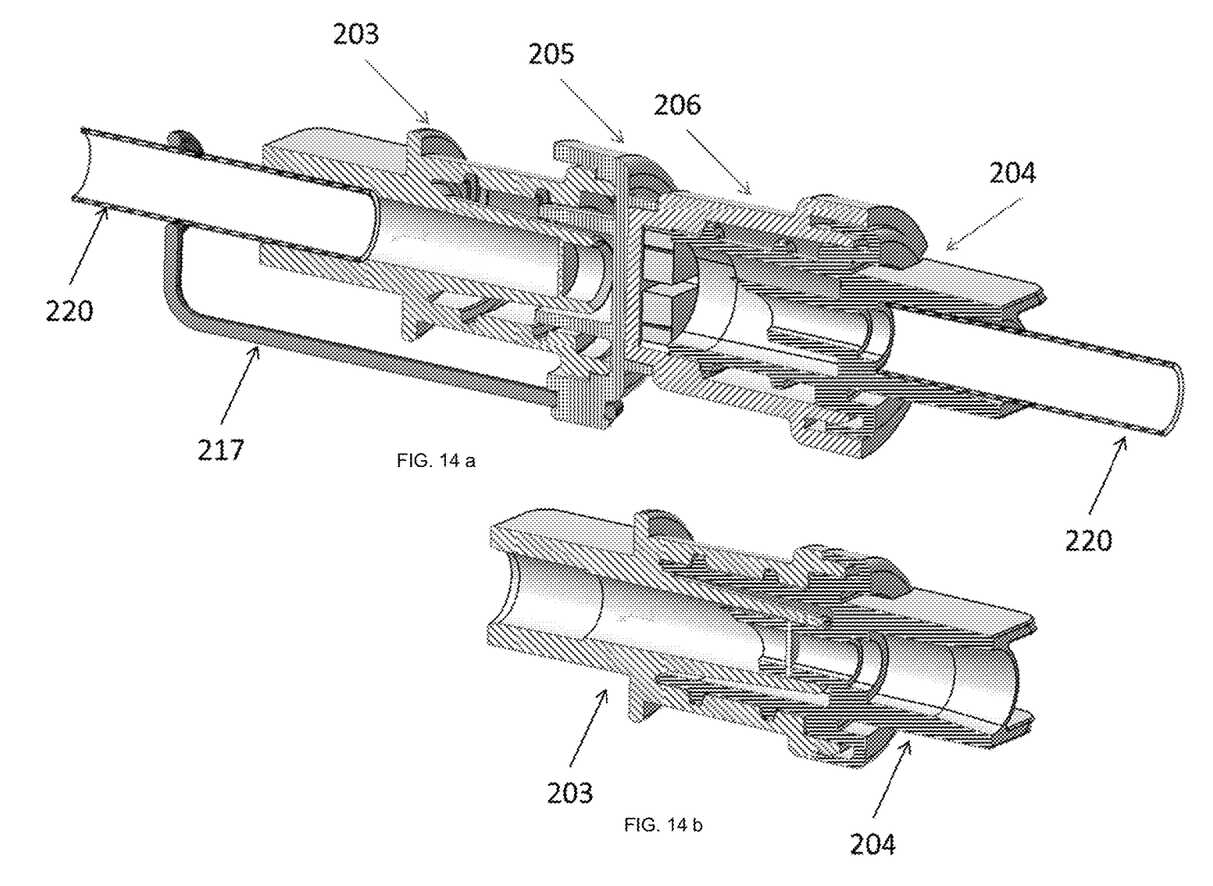
FIGS. 14a and 14b show a section of a connection system with a coupled cap and a section of a connection system connected after removing the caps

In an embodiment shown in FIGS. 12 to 14, each connector comprises:
fluid connection means (210),
physical connection means (209),
caps (205, 206).

In one preferred embodiment, for each connector/cap assembly (201, 202), the fluid connection means comprise an opening defining a fluid flow passage (219). This flow passage is in fluid connection with a tube (220) that extends beyond the proximal end of the connector (211). The physical connection means (209) at least partly surround the fluid connection means (210) so that the fluid connection means (210) are at least partly protected by the physical connection means (209). The objective of the fluid connection means is to make it possible to create a continuous fluid flow passage between the first and second connectors. And the physical connection means make a good connection and maintain the connection between the two connectors. The fluid connection means (210) and the physical connection means (209) are preferably firmly and permanently fixed to the body (207) of the connector. The body (207) of the connector may be formed of a single part comprising the fluid connection means (210) and the physical connection means (209). The cap (205, 206) is fashioned to protect and/or surround the fluid connection means (210) and the physical connection means (209).

The embodiment of FIGS. 12 to 14 therefore makes possible numerous advantage as much at the level of guaranteed sterility as at the level of the cost of manufacturing and using the connector.

In one embodiment, the system comprises a connector defining male type physical connection means while the compatible connector comprises female type physical connection means. Similarly, the system comprises a connector defining male type fluid connection means while the compatible connector comprises female type fluid connection means. The connectors preferably comprise physical and fluid connection means of the same type.

At least one of the physical connection means projects relative to the fluid connection means and comprises an internal surface defining a safety enclosure. In other words, at least one of the two physical connection means surrounds and extends beyond the fluid connection means in order to define a safety enclosure. The external surface of the female type physical connection means is preferably in direct contact with the exterior environment.

As FIG. 14b shows, when the connectors are connected, the various connection means are therefore telescoped with respect to each other in order to improve the sealing of the connection system and/or in order to guarantee the sterility of the flow passage. The physical connection means of the first connector (203) therefore surround and protect the physical connection means of the second connector (204) which in turn surround and protect the fluid connection means of the first connector (203) which in turn surround and protect the fluid connection means of the second connector (204). In other words, the male type fluid connection means enter the female type fluid connection means which enter the male type fluid connection means which enter the female type connection means.

In one embodiment, the cap (205) of the first connector (203) may comprise a projecting internal element for at least partially surrounding the fluid connection means (210) of the first connector (203).

In one embodiment, the physical connection means (209) comprise a compatible thread system disposed on and/or in the body of the connectors. In particular, the thread system of the first connector is arranged on an interior part of its physical connection means and the thread system of the second connector is arranged on an exterior part of its physical connection means.

In order to prevent the caps falling to the floor when they are removed from the connectors, at least one of the connector/cap pairs comprises a retaining device (217) connecting a connector to its cap. If the cap coupling means allow it, the other cap having no retaining device is secured to the cap connected to said retaining device (217). However, it is important that this retaining device (217) be designed to allow the cap to move sufficiently far away from the fluid connections, in other words from the safety enclosure.

In accordance with one embodiment, the two compatible connectors (203, 204) are manufactured from a material not having the same physical characteristics. For example, the second connector is manufactured from a relatively harder material than the first connector. This makes it possible to create stresses increasing the friction forces in order to guarantee good retention and/or some degree of sealing when the connectors are connected to each other.

In accordance with one embodiment, the connector and the cap are manufactured from a material not having the same physical characteristics. For example, the second connector is relatively harder than its cap. This makes it possible to create stresses increasing the friction forces in order to guarantee good retention when the cap is locked onto its connector.

In accordance with this same principle, the first connector is therefore manufactured from a relatively softer material than its cap and the second connector. The second connector is manufactured from a relatively harder material than its cap and the first connector. To facilitate and enhance the cooperation of the coupling means of the caps, the cap of the first connector may be manufactured from a relatively harder material than the cap of the second connector. Similarly, the first connector and the cap of the second connector (reciprocally: the second connector and the cap of the first connector) may have identical physical characteristics and they may be characterized by a substantially equal level of hardness.

The invention claimed is:

1. A connector system comprising two connectors for connecting two fluid lines together, each connector comprising:
 a distal end for connecting to the other connector,
 a proximal end connected to a respective fluid line,
 a fluid flow passage in fluid connection with the respective fluid line arranged at the distal end,
 a physical connection element for connecting the respective connector to the other connector,
 a cap configured to be placed at the distal end of the respective connector, the cap configured to protect the respective fluid flow passage of the respective connector to prevent an interconnection between the two connectors while the cap is engaged to the distal end of the respective connector, each cap having a coupling device configured to couple the respective cap to the other cap,
 a locking device for firmly holding the respective cap to the respective connector, and
 a release mechanism to unlock the locking device to allow a removal of the respective cap from the respective connector when the two caps are coupled to each other without that the user touches the two caps.

2. The system as claimed in claim 1, wherein the two caps are configured to protect the respective physical connection element of the respective connector.

3. The system as claimed in claim 1, wherein each connector includes a fluid connection element defining the respective fluid flow passage, wherein each cap surrounds and protects the respective fluid connection element.

4. The system as claimed in claim 3, wherein each physical connection element surrounds and extends beyond the distal end of the respective fluid connection element.

5. The system as claimed in claim 1, wherein the fluid and physical connection element are adapted to be connected at a same time.

6. The system as claimed in claim 1, wherein, for each connector, the fluid connection element and the physical connection element are fastened together.

7. The system as claimed in claim 1, wherein one of the two connectors comprises a male type fluid connection element and the other one of the two connectors comprises a female type fluid connection element.

8. The system as claimed in claim 1, wherein one of the two connectors comprises a male type physical connection element and the other one of the two connectors comprises a female type physical connection element.

9. The system as claimed in claim 1, wherein one of the two connectors comprises a male type physical and fluid connection element and the other one of the two connectors comprises a female type physical and fluid connection element.

10. The system as claimed in claim 1, wherein the coupling device enables an uncapping of the respective connector.

11. The system as claimed in claim 1, wherein the connectors can be uncapped only when the caps are coupled by the respective coupling device.

12. The system as claimed in claim 1, further comprising a drive element for at least partly moving the respective cap away from the respective connector when the locking device is deactivated.

13. The system as claimed in claim 1, wherein the coupling device of each cap includes a coding system so that only compatible codings enable a coupling of the caps to each other.

14. The system as claimed in claim 13, wherein the coupling device of a cap are compatible with the coupling device of only one cap or of a plurality of caps so that certain connector/cap pairs are compatible with a series of other connector/cap pairs.

15. The system as claimed in claim 1, wherein the locking device includes a thread system disposed on at least one of the respective cap and the respective connector.

16. The system as claimed in claim 1, wherein the locking device includes a lug.

17. The system as claimed in claim 1, wherein the locking device includes a slot.

18. The system as claimed in claim 1, wherein the locking device includes a safety element preventing unintentional deactivation of the locking device.

19. The system as claimed in claim 18, wherein the safety element includes a leaf spring on which a projecting element is configured to immobilize the locking device at least temporarily.

20. The system as claimed in claim 18, wherein the safety element is deactivated by applying a minimum force.

21. The system as claimed in claim 18, wherein the safety element is configured to prevent locking of the connector again after unlocking it.

22. The system as claimed in claim 1, wherein
 the release mechanism is configured to be activated by a trigger.

23. The system as claimed in claim 22, wherein the trigger is arranged on at least one of the cap and the connector.

24. The system as claimed in claim 1, wherein one of the two connectors is made of a relatively softer material than a material of the other one of the two connectors.

25. The system as claimed in claim 1, wherein one of the caps is made of a relatively softer material than a material of the other one of the caps.

26. The system as claimed in claim 1, wherein at least one of the two caps is made from a relatively softer material than the respective connector.

27. The system as claimed in claim 1, wherein at least one of the two locking devices a thread system arranged at the respective connector.

28. The system as claimed in claim 1, wherein at least one of the two connectors comprises a retaining device connecting the connector to the respective cap, the retaining device enabling the respective cap to be held near the one of the two connectors after deactivation of the locking device.

29. The system as claimed in claim 1, wherein at least one of the two connectors comprises a membrane situated in the flow passage;
 wherein the other one of the two connectors comprises a spike adapted to open the membrane at a time of connecting the connectors.

30. A method of removing two caps from two connectors, respectively, without manipulating the two caps, the method comprising the steps of:
 a. holding the connectors by their body,
 b. bringing the two caps into contact,
 c. unlocking a locking device by a release mechanism to allow a removal of a respective cap from a respective connector when the two caps are in contact with each other by step b, and d. moving the two connectors away from each other so that the two caps are detached from the two connectors, respectively.

31. The method as claimed in claim 30, further comprising the step of:

e. coupling the caps by at least one of a coupling device and a coding device.

32. A connector for interconnection with another connector that form a fluid line when interconnected together, the connector comprising:

a connector body, an interconnection element for connecting the connector to the other connector, a cap configured to be placed on the interconnection element to protect a fluid connection and prevent an interconnection between the interconnection element with the other connector while the cap is engaged to connector, the cap having a coupling device configured to connect the cap to a cap of the other connector;

a locking device for removably holding the cap to the connector, and a release mechanism to unlock the locking device to allow a removal of the cap from the connector when the coupling device and the other coupling device are connected to each other.

33. The connector according to claim 32, where the release mechanism is configured to unlock the locking device without a need of the user to touch the cap.

* * * * *